United States Patent [19]

Green et al.

[11] Patent Number: 5,339,870
[45] Date of Patent: Aug. 23, 1994

[54] STERNUM BUCKLE AND APPLIER

[75] Inventors: David T. Green, Westport; Thomas W. Alesi, Jr., New Fairfield; Henry Bolanos, East Norwalk, all of Conn.; Kenneth E. Toso, Portchester, N.Y.

[73] Assignee: United States Surgical Corporation, Norwalk, Conn.

[21] Appl. No.: 959,325

[22] Filed: Oct. 9, 1992

[51] Int. Cl.$^5$ .................................................. B25B 25/00
[52] U.S. Cl. ................................. 140/123.5; 606/139
[58] Field of Search .............. 606/139, 142, 157, 203; 24/68 CD, 265 CD, 69 CT; 81/9.3; 140/123.5

[56] References Cited

U.S. PATENT DOCUMENTS

| | | | |
|---|---|---|---|
| 1,717,766 | 6/1929 | Eimler | 606/74 |
| 1,950,799 | 3/1934 | Jones | 606/74 |
| 2,622,292 | 12/1952 | Pehaczek . | |
| 2,948,939 | 8/1960 | Prete, Jr. . | |
| 2,987,062 | 6/1961 | Ellison . | |
| 3,111,945 | 11/1963 | Von Solbrig | 606/74 |
| 3,469,573 | 9/1969 | Florio | 606/74 |
| 3,473,528 | 10/1969 | Mishkin et al. . | |
| 3,570,497 | 3/1971 | Lemole . | |
| 3,577,601 | 5/1971 | Mariani . | |
| 3,798,711 | 3/1974 | Cousins . | |
| 3,802,438 | 4/1974 | Wolvek . | |
| 4,035,877 | 7/1977 | Brownson et al. | 24/230 SL |
| 4,037,603 | 7/1977 | Wendorff . | |
| 4,069,554 | 1/1978 | Minolla et al. . | |
| 4,119,091 | 10/1978 | Partridge . | |
| 4,136,422 | 1/1979 | Ivanov et al. . | |
| 4,201,215 | 5/1980 | Crossett et al. . | |
| 4,208,770 | 6/1980 | Takada . | |
| 4,263,904 | 4/1981 | Judet . | |
| 4,279,248 | 7/1981 | Gabbay . | |
| 4,371,192 | 2/1983 | Alix . | |
| 4,386,452 | 6/1983 | Stephenson . | |
| 4,387,489 | 6/1983 | Dudek . | |
| 4,512,346 | 4/1985 | Lemole . | |

(List continued on next page.)

FOREIGN PATENT DOCUMENTS 3244680 6/1984 Fed. Rep. of Germany ........ 606/74
9210460 8/1992 France .

*Primary Examiner*—Tamara L. Graysay

[57] ABSTRACT

An apparatus for applying a buckle assembly about split portions of tissue is provided. The apparatus is particularly contemplated for use with a buckle of the type having a base member with an opening extending generally transversely therethrough for reception of a first strap end portion and a clamp member slidably housed within a channel formed in the base member. The apparatus includes a frame member, a mechanism disposed in a lower surface of the frame member for releasably supporting the buckle member and a mechanism associated with the frame member for advancing the clamp member within the channel of the buckle to a strap securing position wherein the strap member is secured within the buckle member in a looped configuration about the tissue portions.

In an alternate embodiment, a surgical system for repair of split portions of tissue includes a flexible strap member having a buckle member attached thereto. The buckle member includes a base member having a transverse opening extending therethrough for reception of a first end portion of the strap member, a clamp member slidably housed within a partial longitudinal channel defined between lower and upper surfaces of the base member and a tab member for retaining the clamp in a secured position. The buckle may also include a clip member pivotally mounted to an upper surface of the base member to assist in securing the strap member. The system also includes an applier mechanism having a frame, a mechanism disposed in a lower surface of the frame for releasably mounting the buckle and a mechanism for advancing the clamp member within the partial longitudinal channel of the buckle to an engaged position whereby the clamp member securely wedges the strap against the base member.

15 Claims, 9 Drawing Sheets

U.S. PATENT DOCUMENTS

| | | |
|---|---|---|
| 4,535,764 | 8/1985 | Ebert . |
| 4,551,889 | 11/1985 | Narayan et al. . |
| 4,583,541 | 4/1986 | Barry . |
| 4,592,355 | 6/1986 | Antebi .................................. 606/157 |
| 4,608,735 | 9/1986 | Kasai . |
| 4,625,717 | 12/1986 | Covitz . |
| 4,643,178 | 2/1987 | Nastari et al. . |
| 4,712,280 | 12/1987 | Fildan . |
| 4,730,615 | 3/1988 | Sutherland et al. . |
| 4,791,709 | 12/1988 | Fildan . |
| 4,792,336 | 12/1988 | Hlavacek et al. . |
| 4,802,477 | 2/1989 | Gabbay . |
| 4,813,416 | 3/1989 | Pollak et al. . |
| 4,825,515 | 5/1989 | Wolterstorff, Jr. . |
| 4,826,250 | 5/1989 | Ibanez . |
| 4,878,271 | 11/1989 | Kitokovsky . |
| 4,896,668 | 1/1990 | Popoff et al. . |
| 4,944,753 | 7/1990 | Burgess et al. . |
| 4,955,913 | 9/1990 | Robinson . |
| 4,966,600 | 10/1990 | Songer et al. . |
| 5,023,980 | 6/1991 | Thomas . |
| 5,048,575 | 9/1991 | Smith . |
| 5,089,012 | 2/1992 | Prou . |
| 5,123,153 | 6/1992 | Krauss . |
| 5,139,498 | 8/1992 | Ley . |
| 5,163,598 | 11/1992 | Peters et al. . |

FIG. 11
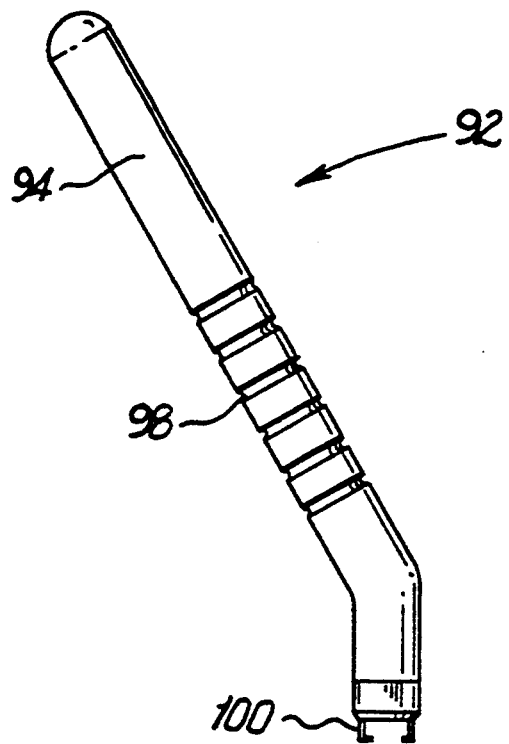
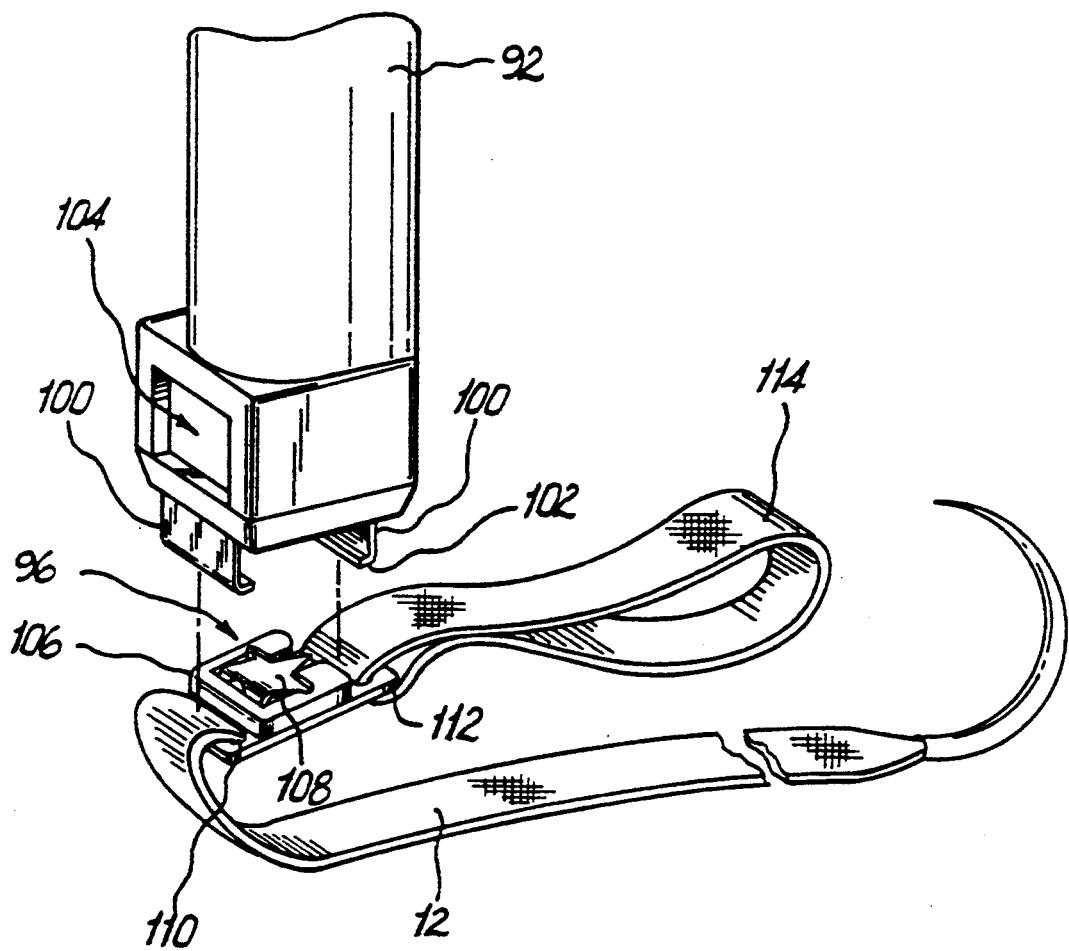
FIG. 12

STERNUM BUCKLE AND APPLIER

BACKGROUND OF THE INVENTION

1. Field of the Invention

The present invention relates to surgical devices for repair of split portions of tissue. In particular, the invention is directed to a sternum buckle applier for applying a buckle with attached strap about split portions of a sternum to maintain the portions in adjacent contacting relationship during healing. The invention is also directed to a buckle for use with the applier.

2. Description of the Prior Art

During surgery that involves a median sternotomy, e.g., open heart surgery, the sternum is split longitudinally to allow access to the organs within the thoracic cavity. Upon completion of the surgery, the sternum is rejoined and closed securely. For proper healing to occur, the split sternum portions are preferably engaged in face-to-face relationship and compressed together while the sternum heals.

Traditional methods for closing a sternum involve securing steel wires around or through the sternum halves and approximating the sternum by twisting the wires together.

Recently, a certain amount of emphasis has been directed towards the use of band or strap assemblies for sternum repair. Such assemblies typically include a locking mechanism which secures a strap in a closed looped configuration about the sternum portions. One example of an assembly of this type is described in U.S. Pat. No. 4,813,416 and includes a banding assembly having a curved surgical needle, an attached thin flat stainless steel band and a buckle mechanism. The sternum halves are brought to abutting closure by looping the band in position around or through the sternum portions and securing the band within the buckle mechanism.

While utilization of steel wires and strap assemblies have been widely accepted for sternum repair, certain shortcomings with these devices are apparent. The use of steel wires presents problems to the surgeon during the operation and to the patient after closure is completed. Steel wires are difficult to maneuver and place around the sternum. The wire edges are often sharp and can easily pierce through undesired areas including tissue surrounding the sternum area or the surgeon's gloves or fingers.

The strap assemblies known heretofore incorporate buckle mechanisms which are relatively structurally complex. For example, the buckle mechanism described in U.S. Pat. No. 4,813,416 includes a saddle part, interned flanges disposed on opposing sides of the saddle part and a loop segment. The saddle part and interned flanges define a band slide through course for reception of a portion of the band. A spring leaf extends upwardly from the loop segment through a slot in the saddle part. The tip end of the spring leaf is narrowed to define a spring tooth or projection which projects through an aperture formed in the band to maintain the closed band loop in a locked configuration.

A further disadvantage of conventional buckle assemblies for sternum closure is that they are generally difficult to apply about the sternum. This difficulty is attributed in part to the relative small size of the buckle, which presents handling and maneuvering problems to the surgeon during use. Further, the locking mechanisms incorporated therein usually involve some form of manual intervention in order to be activated. Since the locking mechanisms are also, accordingly, relatively small in dimension, activation of this mechanism requires precise and delicate maneuvering by the surgeon, which, in effect, manifests in excessive time spent in applying the strap assembly.

Accordingly, it would be desirable to provide a surgical device which assists the surgeon in applying a strap assembly about split tissue portions. The present invention is directed to such a device.

SUMMARY OF THE INVENTION

The present invention is directed to an apparatus for applying a strap assembly about split portions of tissue. The apparatus is contemplated for use with a buckle member of the type having a base member with an opening extending generally transversely therethrough for reception of a first strap end portion and a clamp member slidably housed within a channel formed in the base member. The apparatus comprises frame means, means disposed in a lower portion of the frame means for releasably supporting the buckle member and means associated with the frame means for advancing the clamp member within the channel of the buckle to a strap securing position wherein the strap member is secured within the buckle member in a looped configuration about the tissue portions.

The advancing means comprises a clamping lever pivotally mounted to the frame means and engageable with the clamp member of the buckle. The clamping lever drives the clamp member to the strap securing position upon pivotal movement thereof. The clamping lever includes two separated leg members at one end portion thereof which define an opening therebetween dimensioned for reception of the buckle member. The leg members each have a partial longitudinal groove defined therein. The grooves are correspondingly configured and dimensioned for reception of respective side portions of the clamp member of the buckle member to releasably mount the buckle member to the clamping lever.

The frame means defines an elongated channel in a lower portion thereof in general alignment with the transverse opening formed in the buckle member. The elongated channel defines a passageway for reception and passage of the strap during a strap tightening movement.

The apparatus also includes means disposed in the frame means for securely engaging the strap member received within the elongated channel. The engaging means preferably comprises a resilient retaining lever. The retaining lever is normally biased against the strap to prevent the strap from loosening after a tensioning motion thereof.

The apparatus is also provided with means for disengaging the retaining lever from its engagement with the strap member so that the apparatus may be removed from the strap assembly after activation thereof. The disengaging means comprises a camming pin slidably movable within a camming slot formed in the frame means. The camming pin is advanceable upon pivotal movement of the clamping lever to engage and deflect the retaining lever from the strap member. Preferably, the camming slot includes an offset portion dimensioned to receive and retain the camming pin therewithin such that the retaining lever remains in a deflected position disengaged from the strap member.

The present invention is also directed to an apparatus for applying a strap assembly about split portions of tissue, which strap assembly includes a buckle member and an elongated strap. The apparatus comprises an elongated frame means and means for releasably mounting the buckle member to frame means. The mounting means comprises a pair of opposed resilient leg members extending from a lower surface of the frame means which define a recess therebetween for reception of the buckle member and include inwardly oriented detents at lower end portions thereof. The detents engage with the buckle to releasably mount the buckle to the frame means.

BRIEF DESCRIPTION OF THE DRAWINGS

Preferred embodiments of the invention will be described hereinbelow with reference to the drawings wherein:

FIG. 11 is a side view of another alternative embodiment of the apparatus of the present invention;

FIG. 12 is an enlarged perspective view of the apparatus of FIG. 11 and a preferred buckle member for use with the apparatus.

DETAILED DESCRIPTION OF THE PREFERRED EMBODIMENTS

Figure 1:
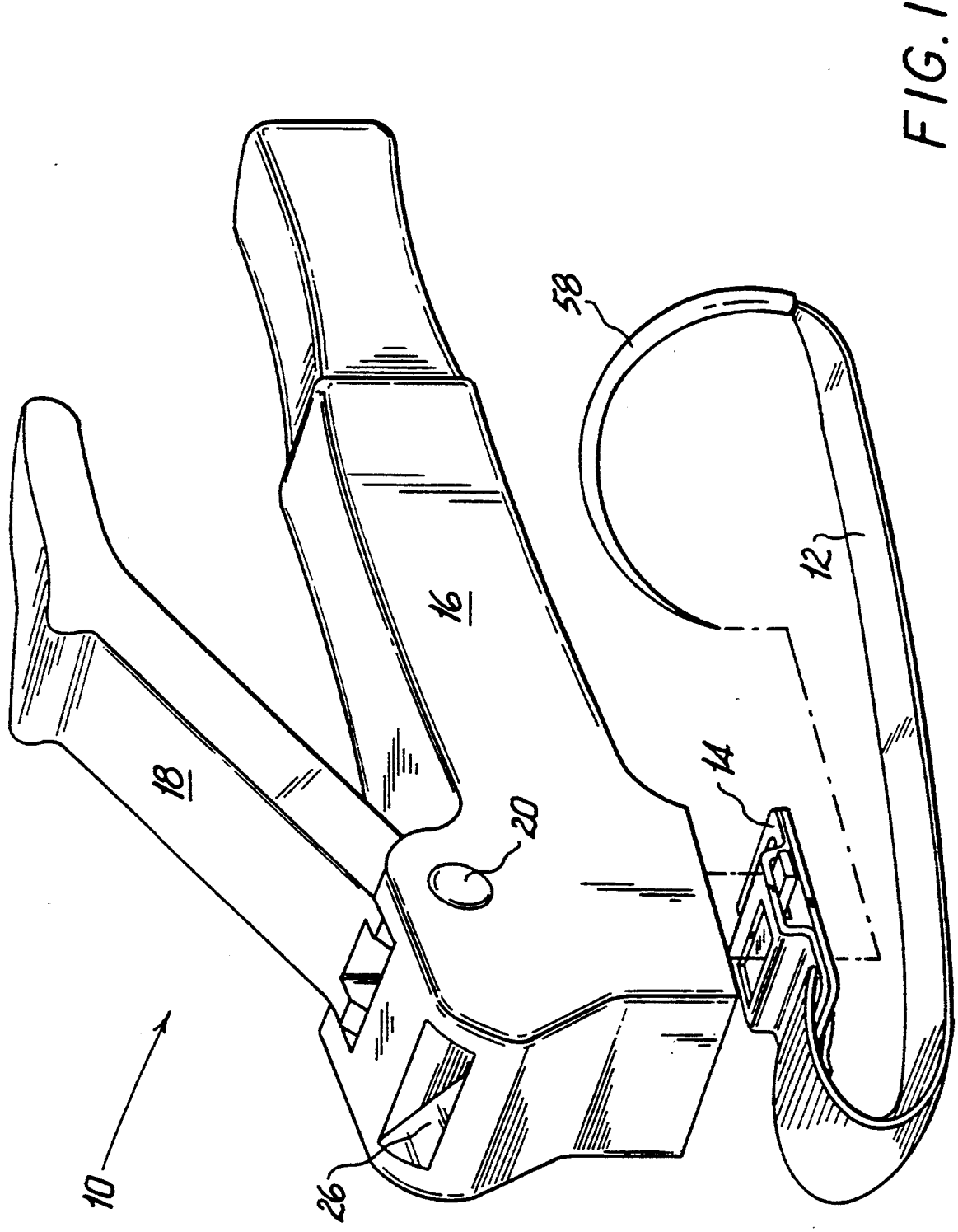
FIG. 1 is a perspective view of the apparatus for applying a strap assembly about split portion of tissue constructed according to the present invention.

Referring initially to FIG. 1 there is illustrated a perspective view of the apparatus 10 constructed according to the present invention. Apparatus 10 is particularly contemplated for use in applying a strap 12 about split portions of tissue such as sternum halves after a sternotomy, although one skilled in the art will readily appreciate the applications for apparatus 10. Strap 12 is secured about the tissue portions by buckle 14 which is initially mounted within apparatus 10. Buckle 14 is specifically configured for operation with apparatus 10 and assumes a locked condition in response to activation of the apparatus.

Figure 2:
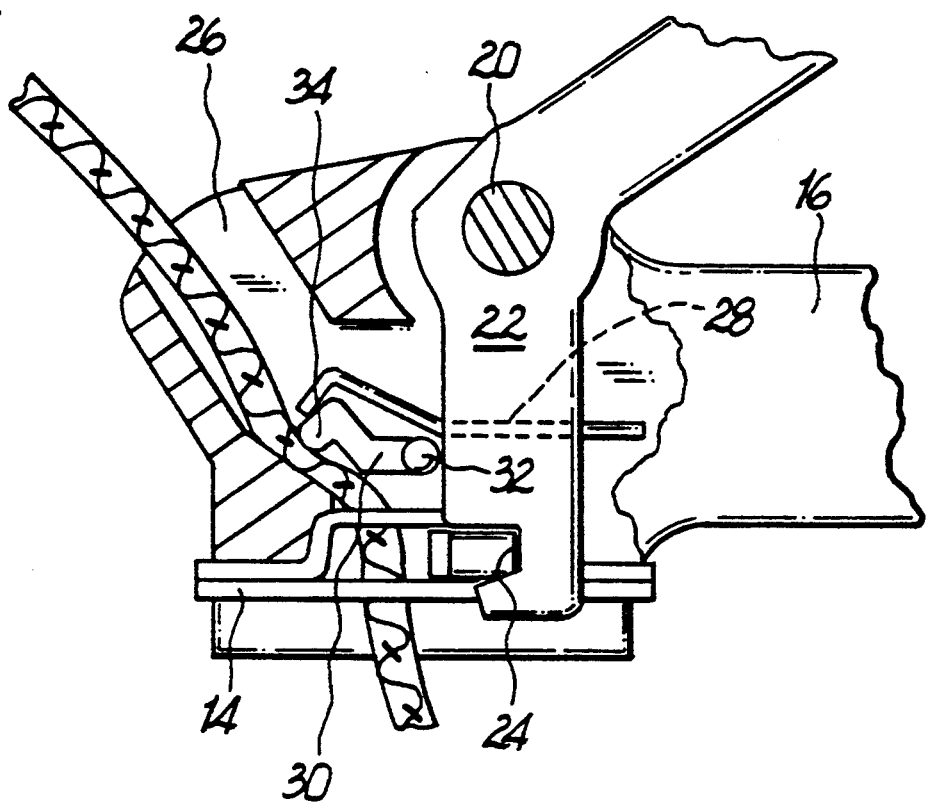
FIG. 2 is a partial side view in cross section of the lower portion of the apparatus of FIG. 1 illustrating the position of the clamping lever prior to activation thereof.
Figure 3:
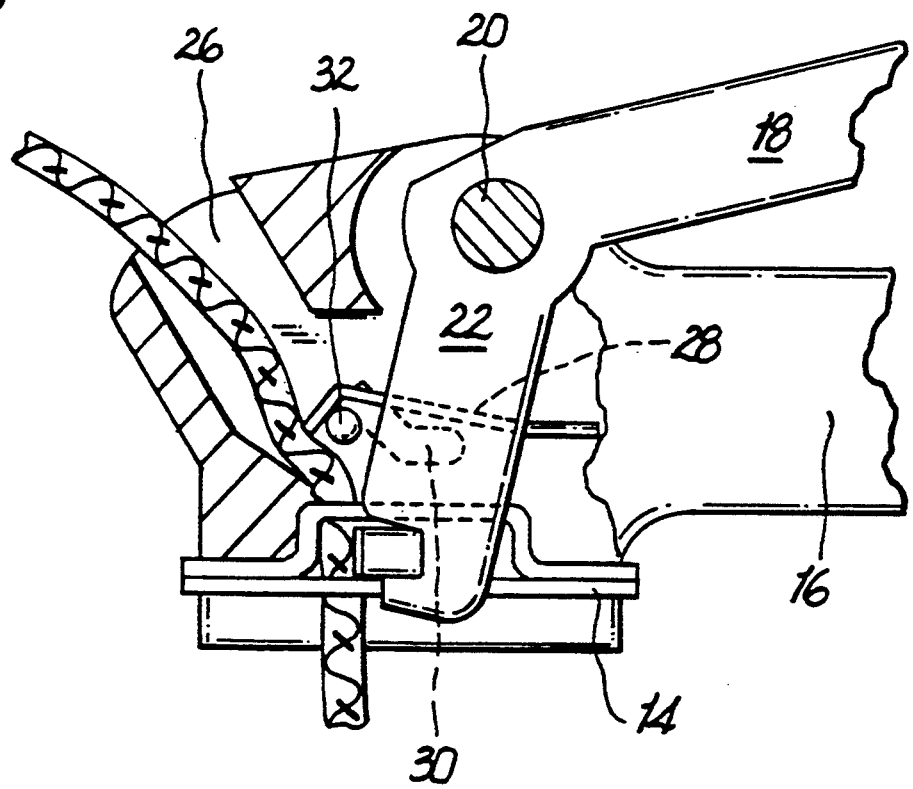
FIG. 3 is a partial side view in cross section of the lower portion of the apparatus of FIG. 1 illustrating the position of the clamping lever after activation thereof.

Referring now to FIGS. 1-3, apparatus 10 includes frame 16 and clamping lever 18 pivotally mounted to the frame via stationary pin 20. Pivotal movement of clamping lever 18 towards frame 16 will cause the lower portion of the lever to pivot towards the forward end of the apparatus to activate the locking mechanism within buckle 14. Clamping lever 18 includes two leg members 22 disposed at a lower portion thereof. Leg members 22 define an opening therebetween particularly dimensioned to receive buckle 14. A partial longitudinal groove 24 (FIG. 4) is formed in each leg member 22. Grooves 24 are dimensioned to receive a clamp member of buckle 14 to mount the buckle to the frame as will be discussed below.

Frame 16 further includes channel 26 which extends from the lower surface of the frame to an upper surface thereof. Channel 26 defines a passageway through frame 16 for strap 12 to pass during tensioning of the strap about the tissue portions. Channel 26 is in general alignment with a strap receiving opening formed in buckle 14.

Referring particularly to FIGS. 2-3, frame 16 also includes a resilient retaining lever 28 pivotally mounted within the frame adjacent channel 26. Retaining lever 28 is strategically positioned to securely engage strap 12 received within channel 26. Retaining lever 28 is adapted to pivot between a generally open position (shown partially in phantom in FIG. 2) to permit passage of strap 12 through channel 26 during a strap tensioning movement and a closed position wherein the forward edge of the lever securely engages the strap to prevent loosening of the strap after a strap tensioning movement. Retaining lever 28 is resiliently biased downwardly so as to assume it closed position after each tensioning movement of strap 12.

Frame 16 also includes camming slot 30 which houses camming pin 32. Camming pin 32 slides within camming slot 30 during pivotal movement of clamping lever 18 towards frame 16. In this advanced position, camming pin 32 engages the forward end portion of retaining lever 28 and lifts the lever from its engagement with strap 12. Camming slot 30 also includes a slightly offset portion 34 (FIG. 2) which receives camming pin 32 after the pin has been advanced by clamping lever 18. As best shown in FIG. 3, camming pin 32 is retained within offset portion 34 of camming slot 30 to maintain retaining lever in a lifted disengaged position so that the apparatus may be removed from strap assembly and the operative site.

Figure 4:
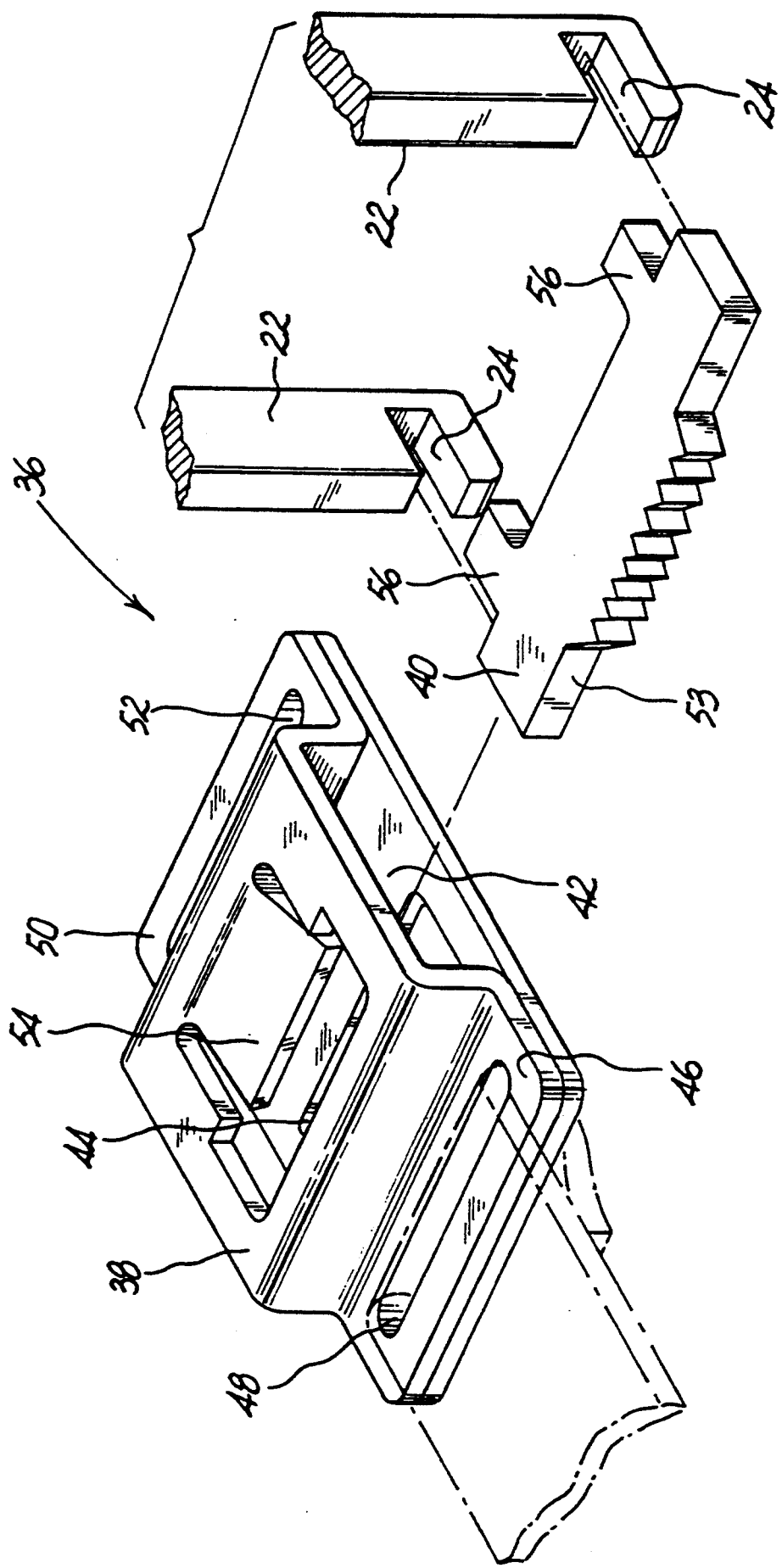
FIG. 4 is a perspective view with parts separated of a preferred buckle assembly for use with the apparatus of FIG. 1.
Figure 5:
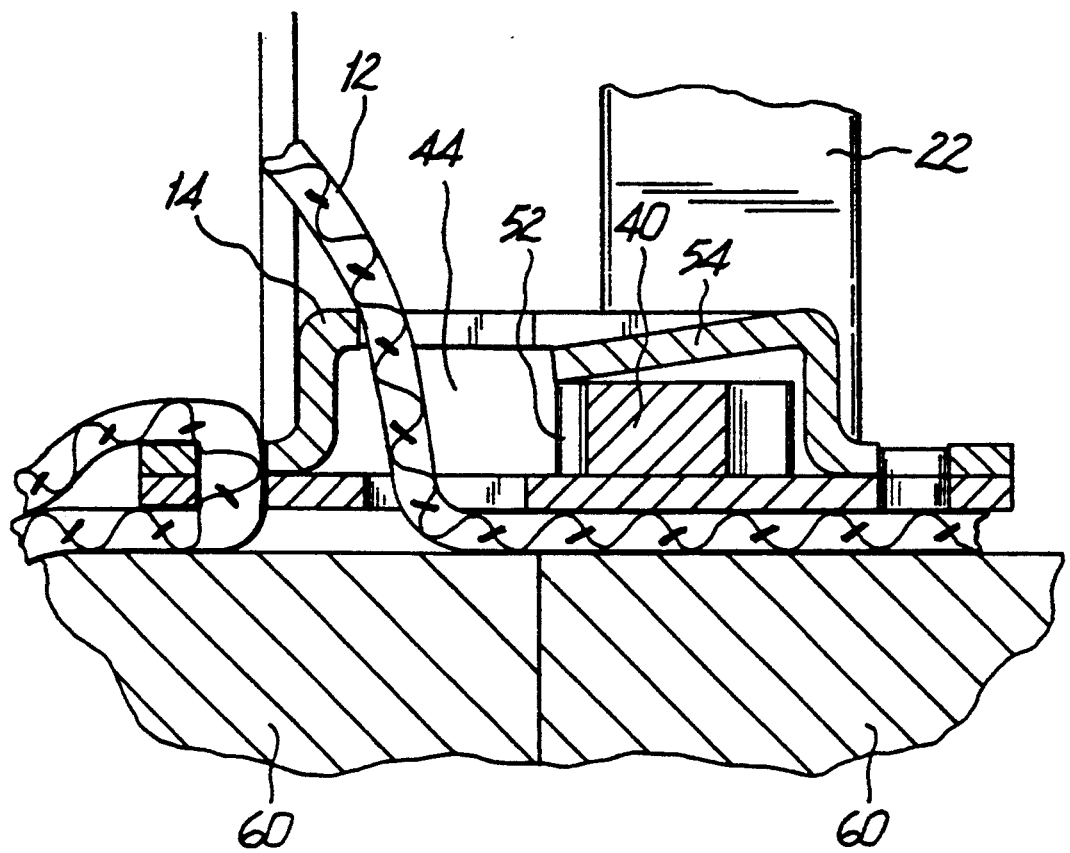
FIG. 5 is a side view in cross section of the buckle assembly in a non-strap engaging position.
Figure 6:
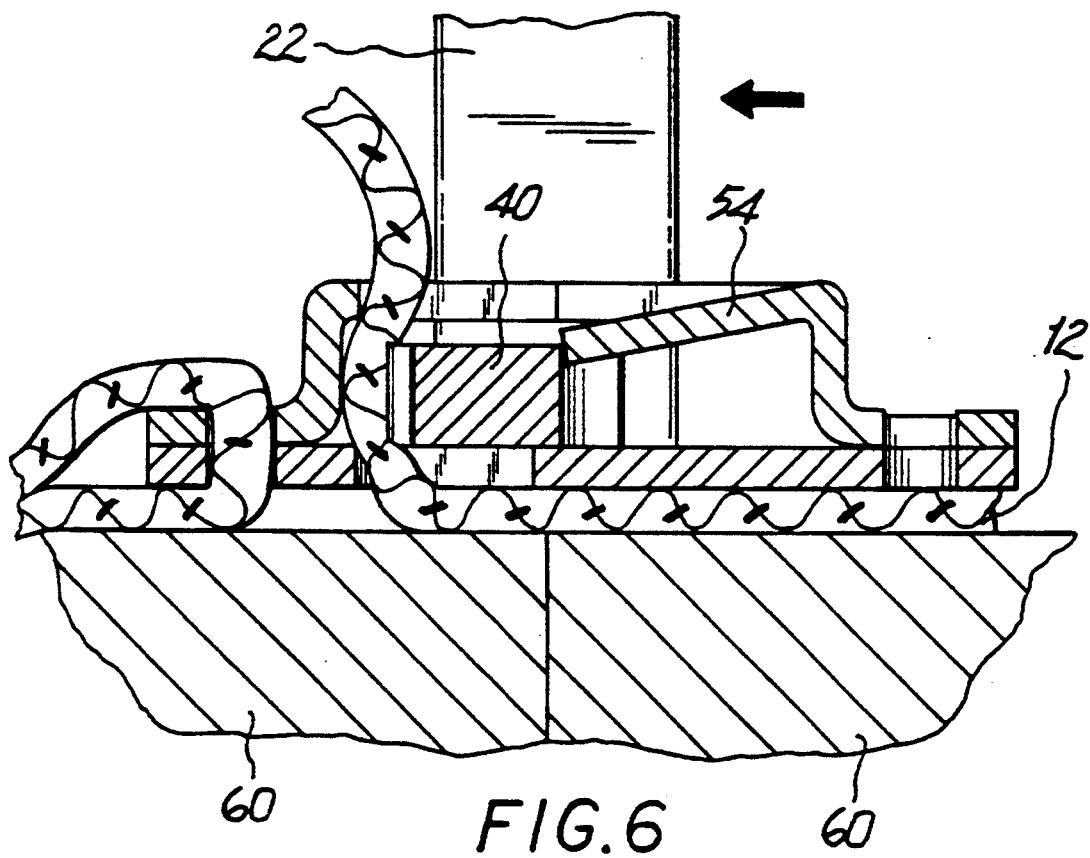
FIG. 6 is a side view in cross section of the buckle assembly in an engaging position after pivotal movement of the clamping lever.

Referring now to FIGS. 4-6, the buckle assembly to be used with apparatus 10 will be described so as to fully appreciate the operation of apparatus 10. Buckle 36 includes base member 38 having a clamp member 40 slidably mounted within a partial longitudinal channel 42 defined between the upper and lower surfaces of the base member. Base member 38 has opening 44 extending generally transversely therethrough for reception of the needled end of strap 12 and an extension 46 having slotted opening 48 for securing the other end of the strap to buckle 14. Base member 38 also includes a second extension 50 having slotted opening 52 to secure a handle to the buckle. A handle, preferably in the form of a looped strap, facilitates maneuvering of buckle 14 about the operative site.

Clamp member 40 is adapted for longitudinal movement within channel 42 from an unadvanced position (FIG. 5) to an advanced strap engaging position (FIG. 6) in response to pivotal movement of clamping lever 18. The forward edge 53 of clamp member 40 is preferably serrated to assist in gripping the wedged strap portion. Clamp member 40 also serves to releasably mount buckle 14 to the apparatus 10. As best shown in FIGS. 2–4, the side portions of clamp 40 extend beyond the sides of buckle 14 and are received within corresponding grooves 24 formed in the lower portion of leg members 22 of clamping lever 18 to mount the buckle to apparatus 10 in a suspended manner. Preferably, clamp member 40 and grooves 24 are correspondingly dimensioned to provide a capturing (loose but secure) fit between the two components.

Referring again to FIGS. 4–6, a downwardly biased resilient tab member 54 partially extends in the upper portion of channel 42. Downwardly biased tab member 54 is configured to engage the rear portion of clamp member 40 to retain the clamp member against strap 12 when the clamp is in the advanced strap engaging position. As shown in FIG. 5, in the unadvanced condition of clamp member 40, downwardly biased tab member 54 rests on an upper surface of clamp member 40. However, once clamp member 40 is moved longitudinally to its advanced position shown in FIG. 6, tab member 54 is released from its contact with the upper surface of the clamp member to assume its normal downwardly biased position. In this position, the forward edge of tab member 54 engages the rear edge of clamp member 40 to securely retain the clamp against strap 12. It is to be appreciated that downwardly biased tab member 54 is configured and dimensioned so as to securely retain clamp member 40 in a wedging locking engagement against the strap without damaging or weakening the strap. Clamp member 40 also includes two leg portions 56 (FIG. 4). Leg portions 56 are engagable with tab member 54 when clamp member 40 is in the advanced strap engaging position of FIG. 6, to thereby minimize transverse movement of the clamp member and potential release of the clamp member through the sides of buckle 14.

The components of buckle 14 are preferably fabricated from a bio-compatible metal such as stainless steel or titanium. Buckle 14 may also be fabricated from polymeric materials including acrylics, polystyrenes, polycarbonates and styreneacrylonitrile (SAN) copolymers and formed by known injection molding techniques.

Strap 12 may be formed of any material suitable for use in stabilizing fractured bones or securing tissue portions generally. Typically, strap 12 may be fabricated from a wide variety of monofilament and braided materials both absorbable and non-absorbable, e.g., catgut, silk, nylon, polyester, polypropylene, linen, cotton and absorbable synthetic materials such as polymers and copolymers of glycolic and lactic acids. Examples of such non-absorbable materials include those fabricated from synthetic fibers such as polyesters, polyethylene, polytetrafluoroethylene and polyamides. A suitable synthetic material includes woven DACRON ™ manufactured by DuPont de Nemours of Wilmington, Del. In the alternative, strap 12 may be formed from a bioabsorbable material such as catgut or synthetic materials including polymers and copolymers of glycolic and lactic acids.

U.S. patent application Ser. No. 07/829,423, filed Feb. 3, 1992, pending the contents of which are incorporated herein by reference, discloses a strap or sternum closure ribbon which may be readily adapted for use with the buckle assembly of the present invention. The strap disclosed in this application is a braided product having a plurality of elongated filamentary reinforcing members of ultra high molecular weight polyethylene fibers. The fibers may be plasma treated to reduce slip characteristics of the yarn. The fibers exhibit strengths from about 375 kpsi (thousands of pounds per square inch) to 560 kpsi and a tensile module of from about 15 msi (millions of pounds per square inch) to about 30 msi.

U.S. Pat. No. 5,019,093 to Kaplan et al. which issued on May 28, 991, the contents of which are also incorporated herein by reference, discloses a suture product which may also be adapted for use with the strap assembly 10 of the present invention. The suture product disclosed in this application is of braided construction and is preferably fabricated from a bioabsorbable polymer such as a glycolide or a lactide. This product exhibits perceptibly enhanced flexibility and hand as well as reduced chatter and drag compared with braided sutures of known construction.

Surgical needle 15 (FIG. 1) may be attached to a first end of strap 12 Needle 58 assists in penetrating the targeted parasternal location and positioning the strap under the sternum and then outwardly at an opposite parasternal location. A curved surgical needle is appropriate for sternum closure and may be securely attached to elongated strap 12 by conventional means. The end portion of strap 12, which is attached to needle, may be tapered to facilitate the needle attachment process.

Further understanding of the apparatus 10 of the present invention will be realized from the description provided of the use of same in securing split portions of a sternum together after a sternotomy.

The application of strap assembly 10 around sternum portions 60 (FIGS. 5–6) to effect sternum closure is accomplished by grasping the needled end of the strap and inserting the needle with attached strap through intercostal tissue between adjacent ribs at a first side of the sternum and then maneuvering the needle under both sternum portions 60 to an opposite parasternal location where it is exposed from the intercostal tissue between the ribs at a second side of the sternum. The needle with attached strap 12 is pulled from the sternum location until a sufficient working length of the strap is provided. The needle is introduced within transverse opening 44 defined in buckle 14 and advanced through the opening and passed through channel 26 of frame 16 (see FIG. 2). The surgeon removes the slack in strap 12 and continues pulling on the strap in a tensioning direction. During advancement of strap 12 through channel 26, retaining lever 28 assumes a generally open position to permit passage of the strap therethrough. However, release of the strap causes lever 28 to assume its downwardly position, to securely wedge the strap against a bearing surface within frame 16 to prevent loosening movement of the strap.

Before completely tightening the strap about the sternum portions, one or more appliers with mounted buckle assemblies may be placed around selected parasternal locations of the sternum in the same manner. When several strap assemblies are in place around the sternum, each member is ready to be tightened. The surgeon proceeds in tensioning strap 12 so as to join the sternum portions in an adjacent face-to-face relationship. Thereafter, the surgeon advances clamping lever 18 towards frame 16 such that leg members 22 of the clamping lever drive clamp 40, which is releasably housed in grooves 24 of the legs, against the strap received within the buckle. Accordingly, tab 54 of buckle 14 is released from its engagement with the upper surface of clamp member 40 and assumes its normal downwardly biased position (FIG. 6) wherein the forward edge of the tab engages the rear edge of the clamp to securely retain the clamp member against the strap portion.

During pivotal movement of clamping lever 18, legs 22 advance camming pin 32 within camming slot 30 such that the pin engages the forward portion of retaining lever to lift the lever from its engagement with strap 12. Pin 32 is received within offset portion 34 to retain the lever in this disengaged position so that the apparatus can be removed from strap 12.

Figure 7:
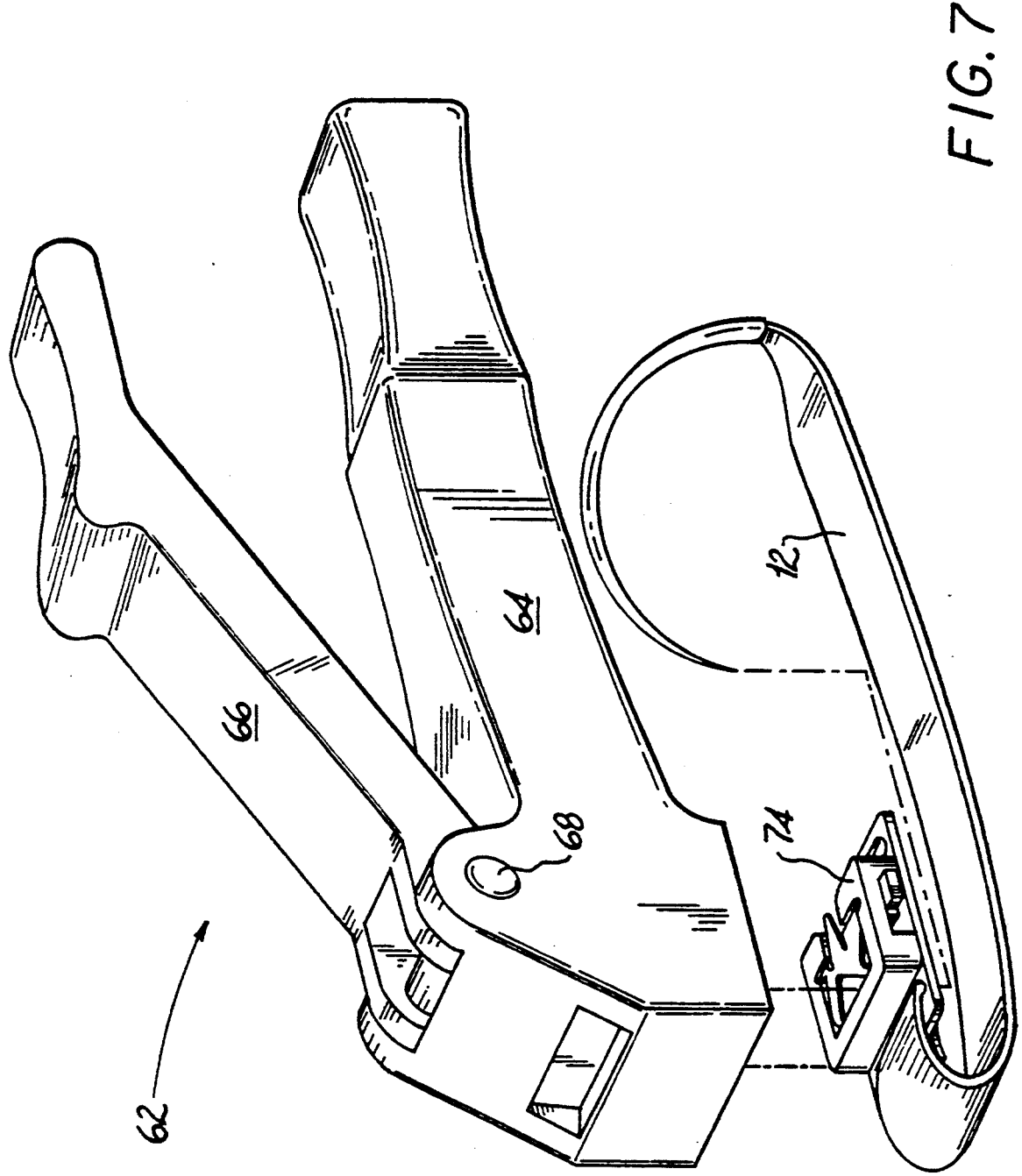
FIG. 7 is a perspective view of an alternative embodiment of the apparatus of FIG. 1.
Figure 8:
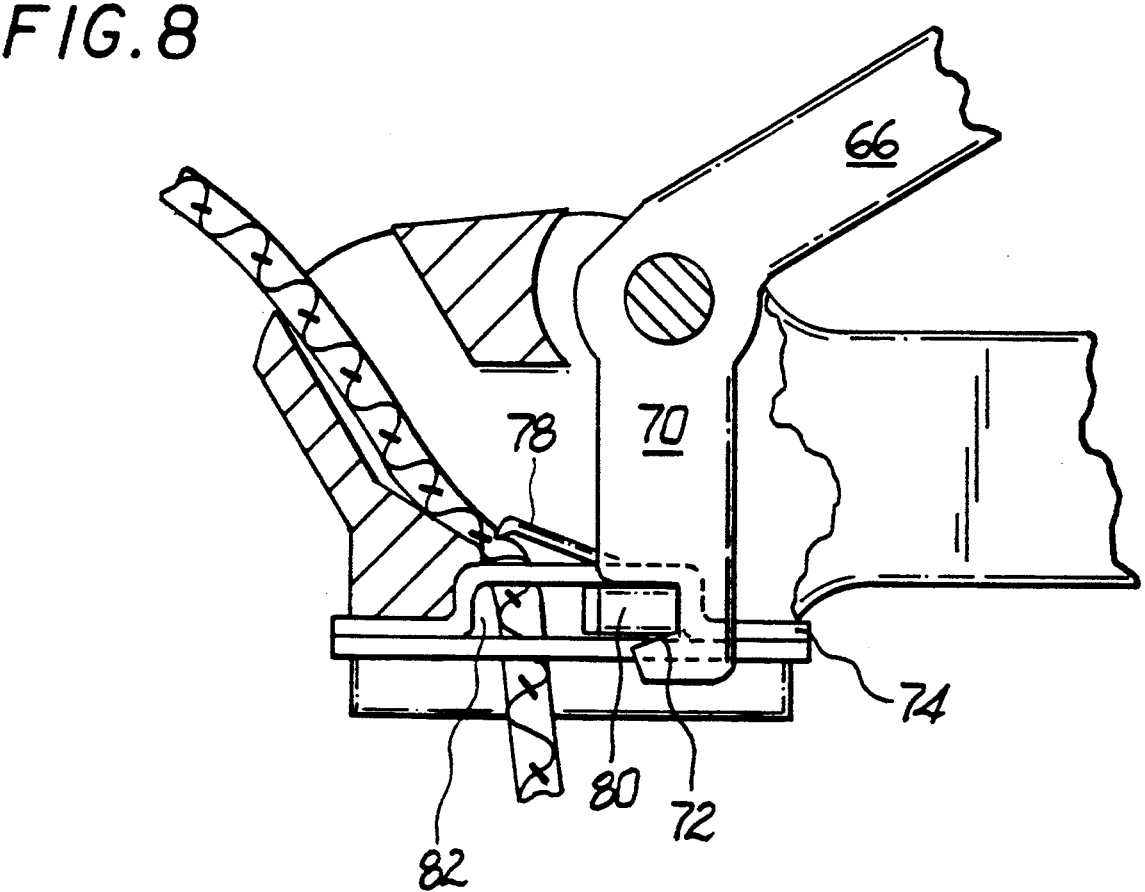
FIG. 8 is a partial side view in cross section of the lower portion of the apparatus of FIG. 7, illustrating the position of the clamping lever prior to activation thereof.
Figure 9:
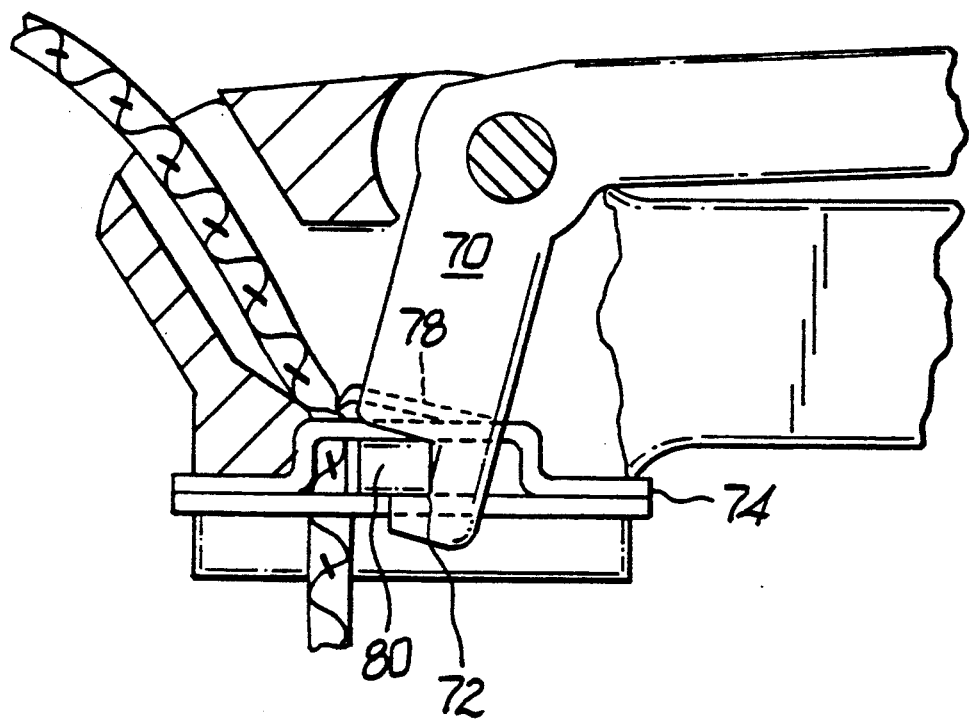
FIG. 9 is a partial side view in cross section of the lower surface of the apparatus of FIG. 7, illustrating the position of the clamping lever after activation thereof.

Referring now to FIGS. 7–9, there is illustrated an alternative embodiment of the apparatus of the present invention. Apparatus 62 is similar in most respects to the embodiment of FIG. 1 except that the retaining lever and camming mechanism have been removed. Apparatus 62 includes frame 64 and clamping lever 66 pivotally mounted to the frame about stationary pin 68. Clamping lever 66 includes leg members 70 (FIG. 8) defining partial grooves 72 for reception of the clamp member of buckle 74. Clamping lever 66 pivots to drive clamp member against the strap received within the buckle in a similar manner as described in the embodiment of FIG. 1.

Figure 10:
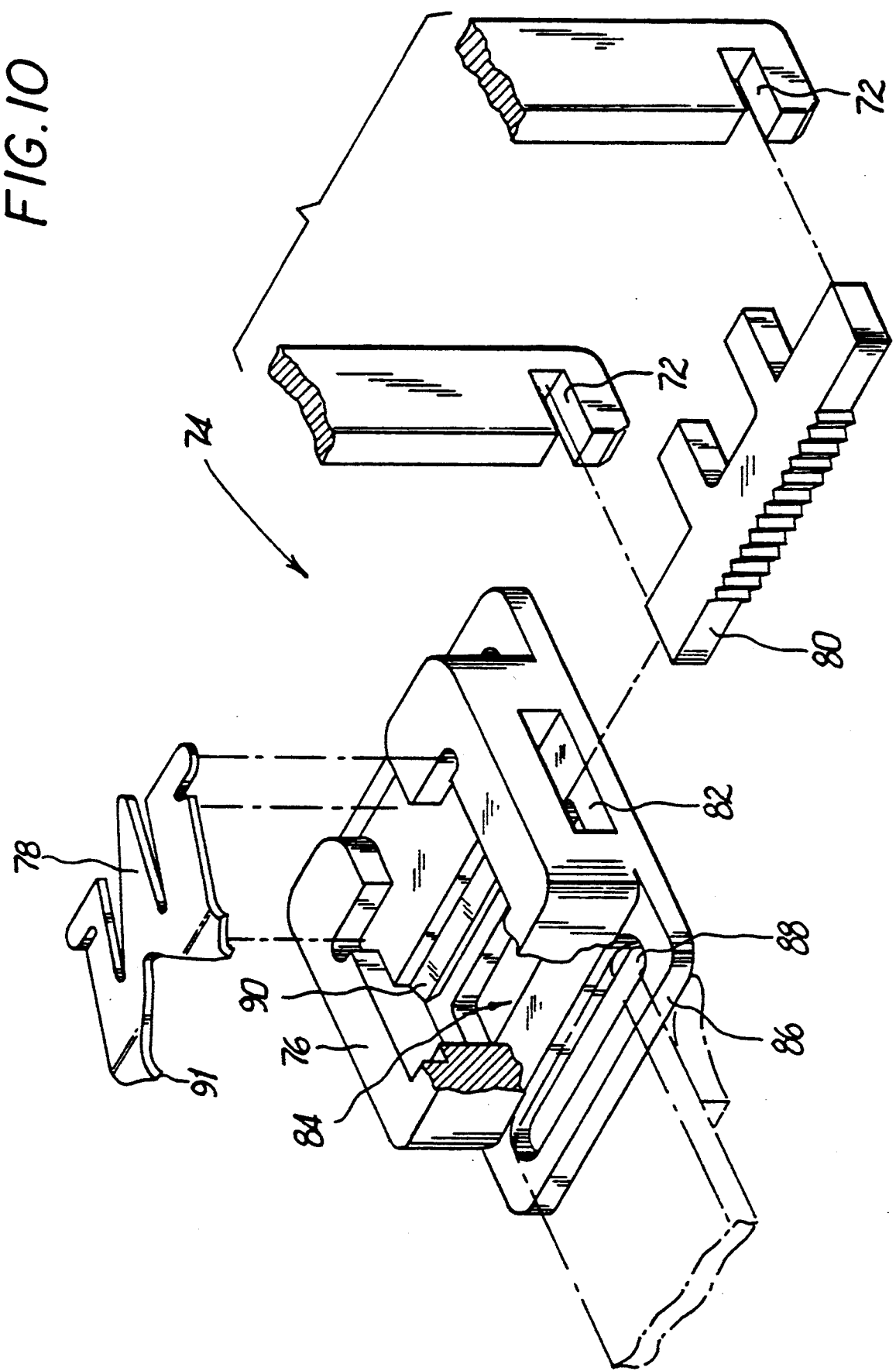
FIG. 10 is a perspective view with pans separated of a preferred buckle assembly for use with the apparatus of FIG. 7.

Referring now to FIG. 10, buckle 74 for use with apparatus 62 of FIG. 7 is illustrated in detail. This buckle is disclosed in commonly assigned copending U.S. patent application Ser. No. 07/959,273 entitled "SURGICAL REPAIR DEVICE" filed on Oct. 9, 1992, pending, the contents of which are incorporated herein and includes base member 76 having clip member 78 pivotally mounted to an upper surface of the base member and a clamp member 80 slidably mounted within a partial longitudinal channel 82 defined between the upper and lower surfaces of the base member. Base member 76 has opening 84 extending therethrough for reception of the needled end of strap 12 and an extension 86 having slot 88 for securing the other end of the strap to the buckle.

Clip member 78 and clamp member 80 both secure strap 12 within buckle 74. In a preferred embodiment, clamp member 80 supplements clip member 78 in securing the strap 12. However, it is to be appreciated that both the clip member and the clamp member are configured and adapted such that each may independently securely lock and wedge strap 12 within buckle 74. In use with the apparatus of FIG. 7, clip member functions similarly to retaining lever 28 of the buckle described in FIG. 2 in that it is resiliently biased downwardly to engage strap 12 received within buckle to prevent loosening of the strap after a tensioning movement thereof.

Clip member 78 is adapted to pivot from an open position to permit passage of the strap through channel of apparatus and a closed position wherein forward toothed 91 edge of the clip member engages the strap. It is to be appreciated that the resilient quality of clip member 78 is sufficient to securely wedge strap 12 against base member 76.

Apparatus 62 is used in the same manner as described in connection with the embodiment of FIG. 1. That is, strap 12 is looped about the sternum and the needled end of the strap is inserted through transverse opening 84 in buckle 74. The strap is tensioned about the tissue portions to a desired tension and then released wherein it is securely engaged by clip 78 to prevent loosening movement thereof. Clamping lever 66 is pivoted clockwise to drive the clamp, which is releasably housed within grooves 72 of legs 70, against the strap and to release the buckle. Downwardly engaging tab member 90 (FIG. 10) disposed within base 76 abuts the rear end of clamp 80 to retain the clamp in the secured position in a similar manner as previously described in connection with the buckle of FIG. 4. The apparatus is then removed from the operative site.

Referring now to FIGS. 11–12, there is illustrated another embodiment of the present invention. Apparatus 92 is contemplated for use in assisting the surgeon in applying a strap assembly about split portions of tissue. Apparatus 92 includes elongated member 94 which releasably mounts a buckle assembly 96 within a housing member 97 disposed at a lower portion of the elongated member. Elongated member 94 is generally bent at a location intermediate first and second ends thereof to present the forward portion of the elongated member in a position in which it can be readily grasped and maneuvered by the surgeon. Preferably elongated member 94 includes serrations 98 to facilitate grasping of the apparatus.

Housing member 97 is rotatably mounted to elongated member 94 to facilitate application of buckle 96 to the operative site. Housing member 97 includes a pair of downwardly extending resilient leg portions 100 at a lower portion thereof which define a space therebetween for reception of buckle 96. Leg portions 100 include inwardly extending detents 102 which engage the lower surface of buckle 96 to mount the buckle to the elongated member to form a snap-lock fit between the two components. Housing member 97 also includes a channel 104 which defines a passageway to receive the strap 12 during tightening of the strap about the tissue portions.

Buckle 96 includes base member 106 having clip member 108 pivotally mounted to an upper surface of the base member by conventional means. Base member 106 has an opening extending transversely therethrough for reception of the needled end of strap and two extensions 110, 112 extending from the front and rear of the base member respectively. Extension 110 has a slot for securing one end of the strap 12 to base member 106. Extension 112 includes a slot which may receive a strap handle 114 as shown. Clip 108 is similar in configuration and operation to that of the corresponding element of the embodiment described in FIG. 10.

Buckle 96 is mounted to elongated member 94 prior to application of the strap assembly about the tissue portions. In particular, downwardly extending leg portions 100 are positioned on the sides of buckle 96 such that detents portions 102 form a snap lock fit to engage the lower surface of base member 106.

In use, apparatus 92 with mounted buckle 96 is applied to the operative site. The needle end of the suture is passed about the tissue portions and then introduced within the transverse opening within buckle 96. The needle and attached strap is advanced through channel 104 of elongated member 94. Strap 12 is tightened to remove the slack and to bring the tissue portions in an adjacent engaged relation. Thereafter the assembly is tightened to a desired tension and the strap is released. The apparatus is then removed from the operative site.

Figure 13:
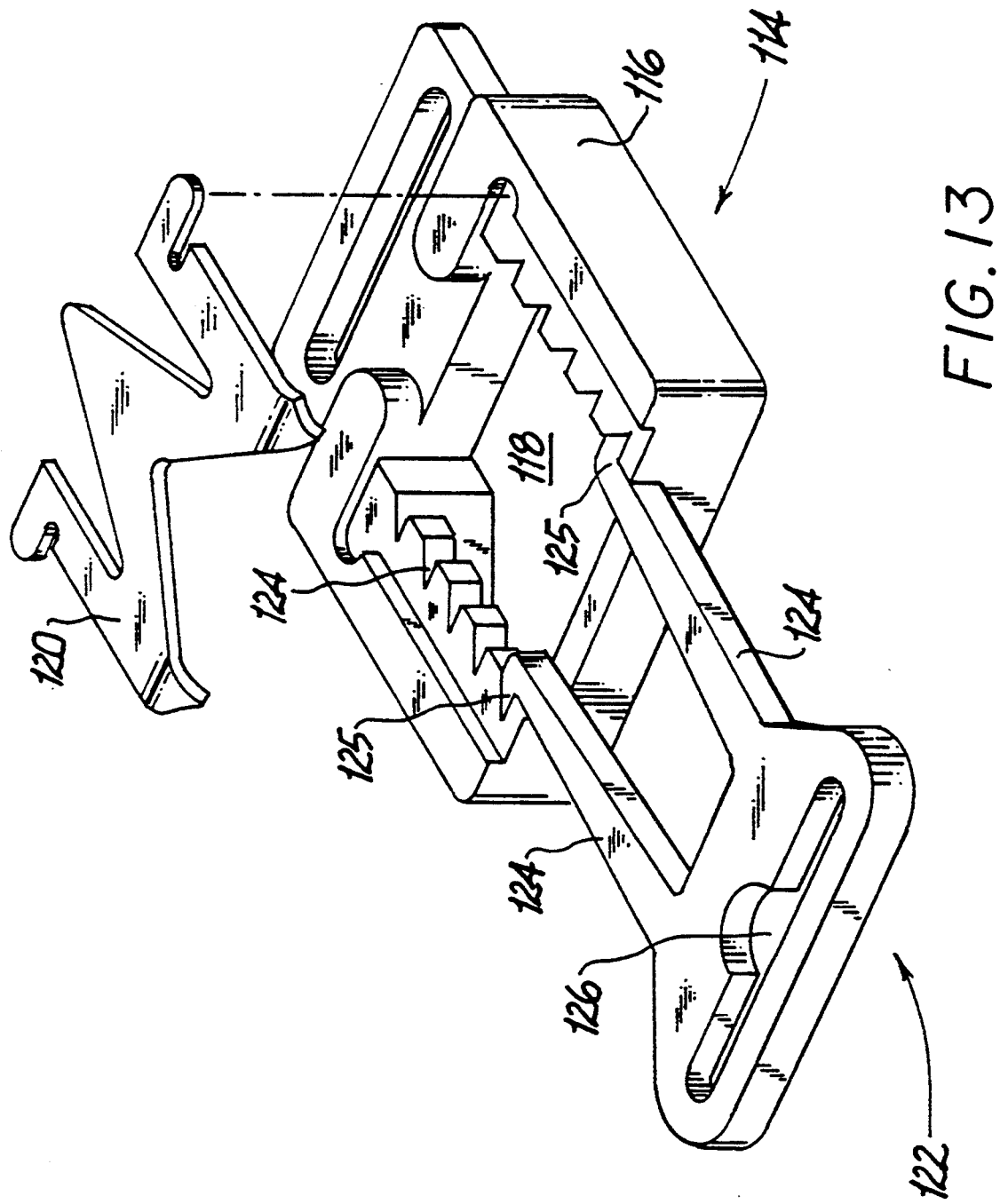
FIG. 13 is a perspective view with parts separated of another preferred buckle which is contemplated for use with the apparatus of FIG. 11.

Referring now to FIG. 13, there is illustrated another alternative buckle assembly which can be used with any of the aforedescribed apparatus, particularly the apparatus of FIGS. 11–12. Buckle 114 includes base member 116 having a transverse opening 118 for reception of the strap and a resilient clip 120 pivotally mounted to the upper surface of the base member. Clip 120 pivots from an open position to permit passage of strap through the buckle and a closed position to securely engage the strap. Buckle 114 is also provided with a strap adjusting member such as generally U-shaped resilient double latch clamp 122 with latching legs 124. Legs 124 include outwardly extending detents 125, which detents mate with corresponding latch engaging portions such as teeth formed within the inner surfaces of base 116. Alternatively, slots or any other suitable engaging portions may also be utilized. Each latching leg is resiliently biased outwardly from the other and must be resiliently deformed when inserted within the buckle. The strap is secured to the U-shaped double latch clamp via slotted opening 126 and is looped about the tissue portions where it is advanced through transverse opening 118 in base 116. The double latch may be advanced within the buckle to tighten the strap around the tissue portions. Double latch is retained in its advanced position by the engagement of latching legs and corresponding teeth formed in the inner surfaces of the buckle.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. An apparatus for applying a strap assembly about split portions of tissue, the strap assembly including a buckle member and an elongated strap, the buckle member being of the type having a base member with an opening extending generally transversely therethrough adapted for reception of a first strap end portion and a clamp member slidably housed within a channel formed in the base member, the apparatus comprising:
   frame means;
   means disposed in a lower portion of said frame means adapted for releasably supporting the buckle member; and
   means associated with said frame means adapted for advancing the clamp member within the channel of the buckle member to a strap securing position whereby the strap member may be secured within the buckle member.

2. An apparatus for applying a strap assembly about split portions of tissue, the strap assembly including a buckle member and an elongated strap, the buckle member being of the type having a base member with an opening extending generally transversely therethrough adapted for reception of a first strap end portion and a clamp member slidably housed within a channel formed in the base member, the apparatus comprising:
   frame means;
   means disposed in a lower portion of said frame means adapted for releasably supporting the buckle member; and
   advancing means associated with said frame means adapted for advancing the clamp member within the channel of the buckle member to a strap securing position wherein the strap member may be secured within the buckle member, said advancing means comprising a clamping lever pivotally mounted to said frame means and adapted for engaging the clamp member of the buckle, said clamping lever adapted for driving the clamp member to said strap securing position upon pivotal movement of said clamping lever.

3. The apparatus according to claim 2 wherein said clamping lever includes two separated leg members at one end portion thereof, said leg members defining an opening therebetween dimensioned for reception of the buckle member, said leg members each having a partial longitudinal groove defined therein, said grooves correspondingly configured and dimensioned for receiving respective side portions of the clamp member of the buckle member and thereby adapted to releasably mount the buckle member to said clamping lever.

4. The apparatus according to claim 2 wherein said frame means defines a channel in a lower portion thereof, said channel defining a passageway adapted for reception and passage of the strap through said frame means during tensioning of the strap about the tissue portions.

5. The apparatus according to claim 4 further comprising means disposed in said frame means adapted for securely engaging the strap member received within said channel.

6. The apparatus according to claim 5 wherein said engaging means comprises a resilient retaining lever disposed adjacent said channel, said retaining lever pivotal between an open position adapted for passage of the strap member through said channel and a closed position adapted to wedge the strap against a bearing surface within said frame means.

7. The apparatus according to claim 6 further comprising means for biasing said retaining lever to its open position.

8. The apparatus according to claim 7 wherein said biasing means comprises a camming pin slidably movable within a camming slot formed in said frame means, said camming pin advanceable upon pivotal movement of said clamping lever to engage and deflect said retaining lever to its open position.

9. The apparatus according to claim 8 wherein said camming slot includes an offset portion dimensioned to receive and retain said camming pin therewithin whereby said retaining lever remains in its open position.

10. A surgical system for repair of split portions of tissue which comprises:
    a flexible strap member;
    buckle means comprising:
       a base member including a transverse opening extending therethrough for reception of a first end portion of said strap member and having a partial longitudinal channel defined between an upper and lower surface thereof;
       clip means pivotally mounted to said upper surface of said base member and movable from an open position to permit reception of said first end portion of said strap member and a closed position to securely wedge said strap member between a forward edge of said clip means and said base member; and
       clamp means slidably housed within said partial longitudinal channel of said base member and movable therewithin from a non-engaging position to an engaging position, said clamp means securely wedging said strap member between a forward edge of said clamp means and said base member when in said engaging position; and applier means, including:
frame means,
means disposed in a lower surface of said frame means for releasably mounting said buckle means; and
means associated with said frame means for advancing said clamp means within said partial longitudinal channel of said buckle means to said engaging position to securely wedge said strap between a forward edge of said clamp means and said base member.

11. The system according to claim 10 wherein said frame means defines a strap receiving channel in general alignment with said transverse opening of said buckle means and adapted to permit passage of said strap member therethrough during a tensioning movement of said strap member.

12. The system according to claim 15 wherein said advancing means comprises a clamping lever means pivotally mounted to said frame means and engageable with said clamp means of said buckle means, said clamping lever means driving said clamp means to the strap engaging position upon pivotal movement thereof.

13. The apparatus according to claim 16 wherein said clamping lever includes two separated leg members at one end portion thereof, said leg members defining an opening therebetween dimensioned for reception of said buckle means, said leg members each having a partial longitudinal groove defined therein, said grooves correspondingly configured and dimensioned for reception of respective side portions of said clamp means of said buckle means to releasably mount said buckle means to said clamping lever means.

14. A surgical system for repair of split portions of tissue which comprises:
a strap assembly including buckle means and an attached elongated strap, said buckle means comprising a base member including a transverse opening extending therethrough for reception of a first end portion of said strap and having a partial longitudinal channel defined between an upper and lower surface thereof, said buckle means further comprising clamp means slidably housed within said partial longitudinal channel of said base member and movable therewithin from a non-strap engaging position to a strap engaging position; and applier means, comprising:
frame means defining a strap receiving channel in general alignment with said transverse opening of said buckle means, said strap receiving channel dimensioned to permit passage of said strap therethrough during a tensioning movement of said strap;
means disposed in a lower surface of said frame means for releasably mounting said buckle means;
means associated with said frame means for advancing said clamp means within said partial longitudinal channel of said buckle means to said strap engaging position to securely wedge said strap between a forward edge of said clamp means and said base member; and
means disposed within said frame means for securely engaging said strap member within said strap receiving channel.

15. The system according to claim 19 wherein said engaging means comprises a resilient retaining lever pivotally mounted within said frame means, said retaining lever being pivotal from an open position to permit reception of said strap member through said strap receiving channel and a closed position to securely wedge said strap member against an inner bearing surface of said frame means.

* * * * *